United States Patent [19]

Crocco et al.

[11] Patent Number: 5,262,550
[45] Date of Patent: Nov. 16, 1993

[54] EPOXIDATION PROCESS USING TITANIUM-RICH SILICALITE CATALYSTS

[75] Inventors: Guy L. Crocco, Wilmington, Del.; John G. Zajacek, Devon, Pa.

[73] Assignee: Arco Chemical Technology, L.P., Wilmington, Del.

[21] Appl. No.: 876,772

[22] Filed: Apr. 30, 1992

[51] Int. Cl.$^5$ .................. C07D 301/12; C07D 303/04
[52] U.S. Cl. ..................................... 549/531
[58] Field of Search ........................... 549/531

[56] References Cited

U.S. PATENT DOCUMENTS

| | | | |
|---|---|---|---|
| 4,410,501 | 10/1983 | Taramasso et al. | 423/326 |
| 4,476,327 | 10/1984 | Neri et al. | 568/678 |
| 4,701,428 | 10/1987 | Bellussi et al. | 502/8 |
| 4,824,976 | 4/1989 | Clerici et al. | 549/531 |
| 4,833,260 | 5/1989 | Neri et al. | 549/531 |
| 4,897,252 | 1/1990 | Cochran et al. | 423/591 |
| 4,937,216 | 6/1990 | Clerici et al. | 502/62 |
| 4,975,266 | 12/1990 | Albal et al. | 423/591 |
| 5,039,508 | 8/1991 | Cochran et al. | 423/591 |

FOREIGN PATENT DOCUMENTS

| | | |
|---|---|---|
| 1001038 | 6/1989 | Belgium . |
| 9262 | 4/1980 | European Pat. Off. .......... 549/531 |
| 190609 | 8/1986 | European Pat. Off. . |
| 311983 | 4/1989 | European Pat. Off. . |
| 315247 | 5/1989 | European Pat. Off. . |
| 315248 | 5/1989 | European Pat. Off. . |

OTHER PUBLICATIONS

Thangaraj et al. [*J. Chem. Soc., Chem. Commun.* 123 (1993)].
Mirajkar et al. [*J. Phys. Chem.* 96, 3073 (1992)].
Huybrechts et al., *J. Mol. Catal.* 71, 129 (1992).
Clerici et al., *J. Catal.* 129, 159 (1991).
Notari, in "Innovation in Zeolite Material Science," Studies in Surface Science and Catalysts, vol. 37, p. 413 (1988).
Thangaraj et al, *J. Catal.* 130, 1 (1991).
Huybrechts et al., *Catalysis Letters* 8, 237 (1991).

*Primary Examiner*—Joseph E. Evans
*Attorney, Agent, or Firm*—Stephen D. Harper

[57] ABSTRACT

Olefins are epoxidized by hydrogen peroxide in the presence of a crystalline titanium silicalite zeolite catalyst having a relatively high titanium content. High yields of epoxides with minimal non-selective loss of either hydrogen peroxide or olefin are realized.

24 Claims, No Drawings

EPOXIDATION PROCESS USING TITANIUM-RICH SILICALITE CATALYSTS

FIELD OF THE INVENTION

This invention relates to methods of epoxidizing olefins so as to obtain products containing epoxide functional groups. In particular, the invention pertains to processes whereby a hydrogen peroxide source is reacted with an ethylenically unsaturated substrate in the presence of a titanium silicalite catalyst containing a high proportion of titanium to yield an epoxide.

BACKGROUND OF THE INVENTION

Epoxides such as ethylene oxide, propylene oxide, 1,2-butene oxide and the like are useful intermediates for the preparation of a wide variety of products. The oxirane functionality in such compounds is highly reactive and may be ring-opened with any number of nucleophilic reactants. For example, epoxides may be hydrolyzed to yield glycols useful as anti-freeze components or reactive monomers for the preparation of condensation polymers such as polyesters.

Polyether polyols generated by the ring-opening polymerization of epoxides are widely utilized as intermediates in the preparation of polyurethane foams, elastomers, sealants, coatings, and the like. The reaction of epoxides with alcohols provides glycol ethers, which may be used as polar solvents in a number of applications.

Many different methods for the preparation of epoxides have been developed. One such method involves the use of certain titanium silicalite compounds to catalyze olefin oxidation by hydrogen peroxide. This method is described, for example, in Huybrechts et al., *J. Mol. Catal.* 71, 129(1992), U.S. Pat. Nos. 4,824,976 (Clerici et al.) and 4,833,260 (Neri et al.) European Pat. Pub. Nos. 311,983, 190,609, 315,247 and 315,248, Belgian Pat. Pub. No. 1,001,038, Clerici et al., J. Catal. 129, 159(1991), and Notari, in "Innovation in Zeolite Material Science," Studies in Surface Science and Catalysis, Vol. 37, p. 413 (1988). The titanium silicalite compounds which have heretofore been found to be useful as epoxidation catalysts are synthetic zeolites corresponding to the general chemical formula

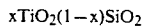

wherein x must be in the range of from 0.0001 to 0.04. Expressed a different way, it has been thought that the molar ratio of Si:Ti must be no less than 24:1 in order for such substances to function effectively a catalysts in the hydrogen peroxide oxidation of olefins to epoxides. The low concentration of titanium in these materials indicates that they are silicalites in which a limited number of titanium atoms have taken the place of silica in the lattice framework. Thus, the titanium atoms are isolated from each other by long

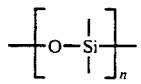

sequences. The prior art teaches that as the proportion of titanium relative to silica in a titanium silicalite is increased, a greater number of titanium atoms in close proximity to other titanium atoms will be present in the lattice framework. Since the epoxidation activity of the titanium silicalite is believed to be due to isolated titanium atoms, whereas the non-selective decomposition of hydrogen peroxide to water and oxygen (i.e., without transfer of oxygen to the olefin) is thought to take place at titanium atoms located in close proximity to each other, the effective use of titanium-rich silicalites as epoxidation catalysts has not heretofore been thought to be feasible. Titanium silicalites containing a relatively high proportion of titanium to silicon would thus have been expected to perform unsatisfactorily in epoxidation reactions since selectivity to epoxide would be significantly lower.

Huybrechts et al. [*J. Mol. Catal.*, 71, 129(1992)], for example, have reported that an attempt to epoxidize 1-octene using hydrogen peroxide and a titanium silicalite containing 4 mole % titanium (Si:Ti=24) gave a total of only 61% selectivity based on hydrogen peroxide to organic oxidation products. The inefficient use of hydrogen peroxide was ascribed to its decomposition to water and oxygen. Higher selectivities were observed using catalysts containing lower levels of titanium. The conversion of 1-octene was also lower than expected from the activity of silicalites containing lower levels of titanium.

The mechanism by which titanium silicalites catalyze the reaction of hydrogen peroxide with organic substrates is not well understood and the outcome of such reactions is highly unpredictable. For example, when an olefin is reacted with hydrogen peroxide in the presence of titanium silicalite, the product obtained may be either epoxide (U.S. Pat. No. 4,833,260), glycol ether (U.S. Pat. No. 4,476,327), or glycol (Example 10 of U.S. Pat. No. 4,410,501).

SUMMARY OF THE INVENTION

Contrary to the expectation of the prior art, it has now been discovered that titanium silicalite zeolites containing high proportions of titanium are extremely productive catalysts for the conversion of ethylenically unsaturated substrates to epoxides using hydrogen peroxide as a source of oxygen. Remarkably high selectivities to epoxide are realized with minimal non-productive hydrogen peroxide decomposition or organic by-product formation.

This invention provides a process for producing an epoxide comprising contacting an olefin with a hydrogen peroxide source in the presence of a catalytically effective amount of a titanium silicalite zeolite having a Si:Ti molar ratio in the lattice framework of said zeolite of from 8:1 to 23:1 for a time and at a temperature effective to convert the olefin to epoxide.

DETAILED DESCRIPTION OF THE INVENTION

In the process of this invention, an olefin is epoxidized using a source of hydrogen peroxide ($H_2O_2$) as an oxidizing agent. It has now been unexpectedly discovered that the use of a titanium-rich silicalite catalyst having a Si:Ti molar ratio in the lattice framework of the catalyst of from 8:1 to 23:1 results in the rapid and highly selective formation of epoxide with minimal loss of the hydrogen peroxide through non-selective decomposition. This discovery was unexpected in view of the teaching of the prior art that titanium silicalites having a high proportion of titanium atoms in close proximity to each other would perform poorly as epoxidation catalysts.

The preparation of titanium silicalites suitable for use in the process of this invention is described, for example, in Thangaraj et al., *J. Catal.* 130, 1(1991), the teachings of which are incorporated herein by reference in their entirety. Typically, a hydrolyzable organosilicate such as tetraalkyl orthosilicate is first partially hydrolyzed by combining with an aqueous solution of a quaternary ammonium salt (preferably, the hydroxide salt). The amount of water employed is from 25% to 75% of the amount theoretically required to completely hydrolyze the organosilicate. The resulting partially hydrolyzed mixture is then combined with a titanium alkoxide or other hydrolyzable titanium compound. The molar ratio of silicon to titanium in the final catalyst may be readily controlled as desired by varying the relative proportions of organosilicate and titanium alkoxide employed. To attain a high degree of titanium incorporation in the lattice framework, it is desirable to dissolve the titanium alkoxide in an anhydrous organic solvent prior to combining with the partially hydrolyzed mixture and to employ a titanium alkoxide such as titanium tetrabutoxide which has a relatively slow rate of hydrolysis. The anhydrous organic solvent may be an alcohol such as isopropyl alcohol. Preferably, the hydrolysis rate of the organosilicate and the titanium alkoxide are substantially equivalent. An additional portion of the quaternary ammonium salt solution is then added to complete the hydrolysis. The alcohol generated during the hydrolysis steps may then be removed by heating at a slightly elevated temperature (e.g., 50°–100° C.) to yield an initial gel. The initial gel is then allowed to crystallize at a temperature of from 125° to 225° C. for a period of 1 to 7 days. The crystalline titanium silicalite thus obtained is thereafter calcined at 450°–650° C. The catalyst may be treated with an alkaline substance or a silylating agent so as to reduce the surface acidity, in analogy to the methods described in U.S. Pat. No. 4,937,216 for low titanium-content titanium silicalites (the teachings of this patent are incorporated herein by reference in their entirety).

The crystal form of the titanium-rich silicalite catalyst may be varied as desired by selecting different quaternary ammonium salts for use during the preparation of said catalyst. As is well known in the art, the pore size, channel structure, and topology of such catalysts and arrangement of metal atoms in the zeolite framework are influenced by the size and shape of the quaternary ammonium salt. The quaternary ammonium salt thus functions as a template or crystal-directing agent and may, for example, be selected from salts wherein the cation is tetra n-propyl ammonium, tetra n-butyl ammonium, tetraethyl ammonium, tetramethyl ammonium, methyl tri-n-butyl ammonium, triethyl methyl ammonium, n-hexyl trimethyl ammonium, trimethyl ammonium, trimethyl neopentyl ammonium, phenyl trimethyl ammonium, benzyl triethyl ammonium, n-dodecyl trimethyl ammonium, benzyl tri-n-propyl ammonium, tetra n-pentyl ammonium, ethyl pyridinium, diethyl piperidinium, tetra-n-hexyl ammonium, tetra-n-octyl ammonium, tetra-n-dodecyl ammonium, trimethyl ethanol ammonium hydroxide, and the like and combinations thereof and well as any other quaternary ammonium salts known in the art to be useful in the preparation of synthetic zeolites or molecular sieves.

Titanium-rich silicalite catalysts particularly preferred for use in the process of this invention include those substances having an MFI structure (i.e., a topology similar to that exhibited by the ZSM-5 aluminosilicate zeolites) as well as substances having an MEL structure (i.e., a topology similar to that exhibited by the ZSM-11 aluminosilicate zeolites). Other useful catalysts include titanium-rich silicalites having CAN, FAU, FER, TON, LTA, MTT, MTW, or MAZ topologies.

Preferably, essentially all of the titanium present is in the zeolite-like lattice framework. The catalyst itself preferably does not contain any appreciable amount of any amorphous phase or a crystalline phase other than the crystalline titanium silicalite phase. As will be explained subsequently, however, the use of a binder or support in combination with the titanium silicalite may be advantageous under certain circumstances.

Catalysts suitable for use in the process of this invention will have a composition corresponding to the following empirical formula

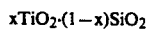

$$xTiO_2 \cdot (1-x)SiO_2$$

where x is between 0.045 and 0.125 (more preferably, between 0.050 and 0.105).

The amount of catalyst employed is not critical, but should be sufficient so as to substantially accomplish the desired epoxidation reaction in a practicably short period of time. The optimum quantity of catalyst will depend upon a number of factors including reaction temperature, olefin reactivity and concentration, hydrogen peroxide concentration, type and concentration of organic solvent as well as catalyst activity. Typically, however, the amount of catalyst will be from 0.01 to 10 grams per mole of olefin. The concentration of titanium in the total epoxidation reaction mixture will generally be from about 10 to 10,000 ppm.

The catalyst may be utilized in powder, pellet, microspheric, monolithic or any other suitable physical form. The use of a binder (co-gel) or support in combination with the titanium-rich silicalite may be advantageous. Supported or bound catalysts may be prepared by the methods known in the art to be effective for zeolite catalysts in general.

Illustrative binders and supports include silica, alumina, silica-alumina, silica-titania, silica-thoria, silica-magnesia, silica-zironia, silica-beryllia, and ternary compositions of silica with other refractory oxides. Also useful are clays such as montmorillonites, koalins, bentonites, halloysites, dickites, nacrites, and ananxites. The proportion of titanium silicalite:binder or support may range from 99:1 to 1:99, but preferably is from 5:95 to 80:20. The methods described in U.S. Pat. No. 4,701,428 (incorporated herein by reference in its entirety) ma be adapted for the preparation of microspheres containing oligomeric silica binder and titanium-rich silicalite crystals which are suitable and preferred for use in the process of this invention.

The olefin substrate epoxidized in the process of this invention may be any organic compound having at least one ethylenically unsaturated functional group (i.e., a carbon-carbon double bond) and may be an aromatic, aliphatic, mixed aromatic-aliphatic (e.g., aralkyl), cyclic, branched or straight chain olefin. Preferably, the olefin contains from 2 to 30 carbon atoms (i.e., a $C_2$–$C_{30}$ olefin). More than one carbon-carbon double bond may be present in the olefin; dienes, trienes, and other polyunsaturated substrates thus may be used. Other examples of suitable substrates include unsaturated fatty acids or fatty acid derivatives such as esters or glycerides and oligomeric or polymeric unsaturated compounds such as polybutadiene.

The olefin may contain substituents other than hydrocarbon substituents such as halide, carboxylic acid, ether, hydroxy, thiol, nitro, cyano, ketone, acyl, ester, anhydride, amino, and the like.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triqlyceride esters), and alkenyl aromatic compounds such as styrene, α-methyl styrene, β-methyl styrene, divinyl benzene, 1,2-dihydronaphthalene, indene, stilbene, cinnamyl alcohol, 2-methyl-1-phenyl-1-propene, 2-methyl-3-phenyl-2-propen-1-ol, cinnamyl acetate, cinnamyl bromide, cinnamyl chloride, 4-stilbenemethanol, ar-methyl styrene, ar-ethyl styrene, ar-tert-butyl styrene, archlorostyrene, 1,1-diphenylethylene, vinyl benzyl chloride, vinyl naphthalene, vinyl benzoic acid, ar-acetoxy styrene, ar-hydroxy styrene (i.e., vinyl phenol), 2- or 3-methyl indene, 2,4,6-trimethylstyrene, 1-phenyl-1-cyclohexene, 1,3-diisopropenyl benzene, vinyl anthracene, vinyl anisole, and the like.

Mixtures of olefins may be epoxidized and the resulting mixture of epoxides either employed in mixed form or separated into the different component epoxides.

The process of this invention is especially useful for the epoxidation of $C_2$–$C_{30}$ olefins having the general structure

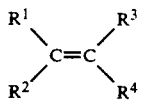

wherein $R^1$, $R^2$, $R^3$, and $R^4$ are the same or different and are selected from the group consisting of hydrogen, $C_1$–$C_{20}$ alkyl, $C_5$–$C_{12}$ alkyl cycloalkyl, $C_6$–$C_{20}$ aryl, and $C_7$–$C_{20}$ aryl alkyl (i.e., an alkyl group bearing at least one aryl substituent such as benzyl or phenethyl).

The oxidizing agent employed in the process of this invention is a hydrogen peroxide source such as hydrogen peroxide ($H_2O_2$) or a hydrogen peroxide precursor (i.e., a compound which under the epoxidation reaction conditions is capable of generating hydrogen peroxide).

The amount of hydrogen peroxide relative to the amount of olefin is not critical, but most suitably the molar ratio of hydrogen peroxide:olefin is from about 100:1 to 1:100 when the olefin contains one ethylenically unsaturated group. The molar ratio of ethylenically unsaturated groups in the olefin substrate to hydrogen peroxide is more preferably in the range of from 1:10 to 10:1. One equivalent of hydrogen peroxide is theoretically required to oxidize one equivalent of a mono-unsaturated olefin substrate, but it may be desirable to employ an excess of one reactant to optimize selectivity to the epoxide. A key advantage of the process of this invention as compared to other epoxidation processes is that neither a large molar excess of hydrogen peroxide relative to olefin or a large molar excess of olefin relative to hydrogen peroxide is required. High yields of peroxide may be realized using a slight (i.e., 5–75%) molar excess of olefin relative to hydrogen peroxide (i.e., the molar ratio of olefin to hydrogen peroxide is from 1.05:1 to 1.75:1). The hydrogen peroxide is thus used in a very efficient manner; little of the hydrogen peroxide is wasted through non-selective decomposition to water (i.e., without oxidation of an olefin molecule). Since hydrogen peroxide is relatively costly to generate, this means that the process of the invention may be economically practiced on a commercial scale. Additionally, processing costs arising from recovering and recycling of olefin are minimized since there is no need to employ a large excess of olefin in order to optimize epoxide selectivity, in contrast to known epoxidation processes employing organic hydroperoxides and molybdenum-containing catalysts.

Although the hydrogen peroxide to be utilized as the oxidizing agent may be derived from any suitable source, a distinct practical advantage of the process of this invention is that the hydrogen peroxide may be obtained by contacting an aryl-substituted secondary alcohol such as α-methyl benzyl alcohol with molecular oxygen under conditions effective to form an oxidant mixture comprised of secondary alcohol and hydrogen peroxide. Typically, such an oxidant mixture will also contain an aryl-substituted ketone such as acetophenone corresponding to the secondary alcohol (i.e., having the same carbon skeleton), minor amounts of water, and varying amounts of other active oxygen species such as organic hydroperoxides. The use of oxidant mixtures of this type in an integrated olefin epoxidation process employing titanium silicalite catalysts is described in more detail in copending United States application Ser. No. 07/876,884, Filed Apr. 30, 1992, entitled "Integrated Process For Epoxide Production".

If desired, a solvent may additionally be present during the epoxidation process of this invention in order to dissolve the reactants other than the zeolite catalyst, to provide better temperature control, or to favorably influence the epoxidation rates and selectivities. The solvent, if present, may comprise from 1 to 99 weight percent of the total epoxidation reaction mixture and is preferably selected such that it is a liquid at the epoxidation reaction temperature. Organic compounds having boiling points at atmospheric pressure of from abut 50° C. to 300° C. are generally preferred for use. Illustrative examples of suitable solvents include, but are not limited to, ketones (e.g., acetone, methyl ethyl ketone, acetophenone), ethers (e.g., tetrahydrofuran, butyl ether), nitrile (e.g., acetonitrile), aliphatic and aromatic hydrocarbons, halogenated hydrocarbons, and alcohols (e.g., methanol, ethanol, isopropyl alcohol, t-butyl alcohol, α-methyl benzyl alcohol, cyclohexanol). More than one type of solvent may be utilized. For example, the use of methanol as a co-solvent when an aryl-substituted secondary alcohol such as α-methyl benzyl alcohol is the main solvent has been found to be particularly advantageous, since even relatively low concentrations (e.g., 5-40 weight % of the total epoxidation reaction mixture) of methanol markedly improve the rate of reaction and epoxide selectivity.

The reaction temperature is not critical, but should be sufficient to accomplish substantial conversion of the olefin to epoxide within a reasonably short period of time. It is generally advantageous to carry out the reaction to achieve as high a hydrogen peroxide conversion as possible, preferably at least 50% and desirably at least 90%, consistent with reasonable selectivities. The optimum reaction temperature will be influenced by catalyst activity, olefin reactivity, reactant concentrations, and type of solvent employed, among other factors, but typically will be in a range of from about 0° C. to 150° C. (more preferably, from about 25° C. to 120° C.). Reaction times of from about 10 minutes to 48 hours will typically be appropriate, depending upon the above-identified variables. Although sub-atmospheric pressures can be employed, the reaction is preferably performed at atmospheric pressure or at elevated pressure (typically, between 1 and 100 atmospheres). Generally, it will be desirable to maintain the reaction components as a liquid phase mixture.

The process of this invention may be carried out in a batch, continuous, or semi-continuous manner using any appropriate type of reaction vessel or apparatus such as a fixed bed, transport bed, stirred slurry, or CSTR reactor. Known methods for conducting metal-catalyzed epoxidations of olefins using hydrogen peroxide will generally also be suitable for use in this process. Thus, the reactants may be combined all at once or sequentially. For example, the hydrogen peroxide may be added incrementally to the reaction zone. Once the epoxidation has been carried out to the desired degree of conversion, the desired epoxide product may be separated and recovered from the reaction mixture using any appropriate technique such as fractional distillation, extractive distillation, liquid-liquid extraction, crystallization, or the like. After separating from the epoxidation reaction mixture by any suitable method such as filtration, the recovered catalyst may be economically re-used in subsequent epoxidations. Similarly, any unreacted olefin or hydrogen peroxide may be separated and recycled. In certain embodiments of the process, the crude epoxidation reaction mixture will also contain an aryl-substituted secondary alcohol or other solvent and possibly a ketone corresponding to the secondary alcohol. After separation of the epoxide from the secondary alcohol and the corresponding ketone, the ketone may be converted back to secondary alcohol by hydrogenation. For example, the ketone may be reacted with hydrogen in the presence of a transition metal hydrogenation catalyst. Hydrogenation reactions of this type are well known to those skilled in the art. The secondary alcohol may also be dehydrated using known methods to yield valuable alkenyl products such as styrene.

From the foregoing description, one skilled in the art can readily ascertain the essential characteristics of this invention, and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

This example illustrates the preparation of a titanium-rich silicalite composition suitable for use in the epoxidation process of this invention and having an MFI crystal structure (topology) A "Teflon" beaker was charged with tetraethyl orthosilicate (Aldrich; 122 g; 0.59 mole) and then fitted with an overhead stirrer. An aqueous solution of tetrapropyl ammonium hydroxide (Aldrich; 170 mL; 1.0M) was added over a 30 min. period and the resulting solution stirred for an additional 30 min. period after addition was completed. A solution of titanium n-butoxide (11.6 g; 0.034 mole) in isopropanol (75 mL) was subsequently added over 45 min. and the mixture stirred for an additional 1.5 hours. Water (150 mL) was thereafter added over a 30 min. period. After transferring to a titanium autoclave, the solution was stirred for 65 hours at 160° C. (78 psig; autogenous). The resulting milky product was removed and the fine solids separated by centrifugation. The centrifuged solids were washed three times with water (300 mL portions), with the washed solids being collected by centrifugation, and then dried at 100° C. for 2 hours. The dried solids were subsequently calcined at 550° C. (the temperature being increased at 10° C./min.) for 5 hours The calcined titanium-rich silicalite catalyst thus obtained had an x-ray diffraction pattern consistent with the presence of an MFI crystalline phase. Elemental analysis found 44 weight percent Si and 5.1 weight percent Ti (Si:Ti mole:mole=15:1), corresponding to the empirical formula:

$$xTiO_2 \cdot (1-x)SiO_2$$

wherein x=0.06.

EXAMPLE 2

This example illustrates a procedure for preparing a titanium-rich silicalite composition useful as an epoxidation catalyst in the process of this invention and having an MEL topology.

The procedure described in Example 1 was repeated, but using tetrabutyl ammonium hydroxide (Aldrich; 170 mL; 1.0M) in place of the tetrapropyl ammonium hydroxide. The calcined titanium-rich silicalite catalyst obtained had an x-ray diffraction pattern consistent with the presence of an MEL crystalline phase. Elemental analysis found 45 weight percent silicon and 4.9 weight percent titanium (Si:Ti mole:mole=16:1), corresponding to the empirical formula:

$$xTiO_2 \cdot (1-x)SiO_2$$

wherein x=0.06.

EXAMPLE 3

A titanium-rich silicalite catalyst containing an MFI crystalline phase and 4.4 weight percent titanium was prepared in accordance with the procedure described in Thangaraj et al., *J. Catal.*, 130, 1(1991). The catalyst (0.73 g) was then charged to a 300 mL glass-lined autoclave together with methanol (25 mL) and then propylene (16 mL; 0.20 mole). The autoclave was equipped with a "Teflon" stir shaft and blade and a "Teflon" tape-wrapped thermowell. After heating the autoclave to 75° C. using an external heating coil, an oxidant mixture containing α-methyl benzyl alcohol, acetophenone, 5.15% hydrogen peroxide, and a minor amount of water (total of 100 mL) which had been prepared by air oxidation of α-methyl benzyl alcohol was then fed into the autoclave over a 15 minute period while constantly stirring the autoclave contents. During the addition, the reaction exothermed to 85° C. The reaction mixture was stirred an additional 30 minutes after addition was completed. After cooling in an ice bath, the contents of the autoclave were analyzed for hydrogen peroxide by iodometric titration and for propylene oxide by gas chromatography. The results obtained were as follows:

Final $H_2O_2$ concentration = 0.11% (0.0040 mole)
$H_2O_2$ conversion = 97%
Propylene oxide produced = 0.12 mole
Selectivity to propylene oxide (based on hydrogen peroxide) = 84%
Selectivity to propylene oxide based on propylene was at least 99%, with a total of less than 1% selectivity to propylene glycol and propylene glycol methyl ethers.

EXAMPLE 4

A 300 mL autoclave was charged with the same titanium-rich silicalite catalyst used in Example 3 (varying amounts), methanol, and propylene as described in Example 3. A mixture of α-methylbenzyl alcohol (70 mL), acetophenone (30 mL), and aqueous 50% hydrogen peroxide (10 mL) was stirred with 30 g $MgSO_4$, filtered, and then fed into the autoclave (preheated to 80° C. using external heating coils) over 38 seconds using an Isco pump attached to the autoclave. The autoclave was open to a reservoir of liquid propylene to obtain pseudo-first order conditions. The temperature was maintained at 80° C. throughout the reaction by internal "Teflon"-lined coils. Samples were removed at 4 minute intervals over 20 minutes and titrated for hydrogen peroxide to obtain the rate data shown below.

| Amount of Catalyst (g) | Ti (ppm) | Rate (hr$^{-1}$) |
| --- | --- | --- |
| 0.73 | 229 | 0.58 |
| 0.35 | 109 | 0.29 |
| 0.23 | 73 | 0.19 |

The rate of reaction was found to be extremely fast and proportional to the titanium concentration in the mixture.

EXAMPLE 5

This example demonstrates the use of methanol as a solvent in accordance with the process of the invention. An autoclave equipped as described in Example 3 was charged with methanol (25 mL) and the same titanium-rich silicalite catalyst (0.73 g) employed in Example 3, followed by liquid propylene (16 mL; 0.20 mole). An attached Isco pump was charged with 100 mL of a solution prepared by mixing methanol (90 mL) and 50% aqueous hydrogen peroxide (10 mL; 0.15 mole $H_2O_2$) The reactor was heated to 63° C. using an external heater, at which point the solution in the Isco pump was added over a period of 15 minutes. During the addition, the contents of the reactor reached a temperature of 78° C. due to the exothermic reaction. After stirring for 30 minutes at 78° C. after addition was completed, the autoclave was cooled with an ice bath and vented. Analysis of the reaction mixture was performed as described in Example 3. The results obtained were as follows:

Final $H_2O_2$ concentration = 0.25% (0.0092 mole)
$H_2O_2$ conversion = 94%
Propylene oxide produced = 0.12 mole
Selectivity to propylene oxide (based on hydrogen peroxide) = 87%

EXAMPLE 6

This example illustrates the epoxidation of allyl alcohol in accordance with the invention. A flask was charged with methanol (18 mL), 50% aqueous hydrogen peroxide (2.8 mL; 0.041 mole $H_2O_2$), allyl alcohol (3.5 mL; 0.051 mole), and the same titanium-rich silicalite catalyst used in Example 3 (0.25 g) and fitted with a reflux condenser. The reaction mixture was heated at 62° C. for 4.5 hours and then analyzed by iodometric titration and gas chromatography. The results were as follows:

Final $H_2O_2$ concentration = 0.42% (0.003 mole)
$H_2O_2$ conversion = 93%
Glycidol produced = 0.029 mole
Selectivity to glycidol (based on hydrogen peroxide) = 76%

The high selectivity to glycidol was unexpected in view of the teaching of the prior art that the reaction of hydrogen peroxide with allyl alcohol in the presence of a titanium silicalite containing a low level of titanium (U.S. Pat. No. 4,410,501; Example 10) yields glycerin and not glycidol.

EXAMPLE 7

A titanium-rich silicalite catalyst having a Si:Ti molar ratio of 10 is prepared in accordance with the teachings of Thangaraj et al., *J. Catal.* 130, 1(1991). The procedure of Example 3 is repeated using this catalyst with the exception that the amount of catalyst is reduced to 0.50 g and the propylene is replaced with allyl chloride (19.3 g; 0.20 moles). Epichlorohydrin is the expected product.

EXAMPLE 8

A titanium-rich silicalite catalyst having a Si:Ti molar ratio of 22 is prepared in accordance with the teachings of Thangaraj et al., *J. Catal.* 130, 1(1991). The procedure of Example 3 is repeated using this catalyst with the exception that the amount of catalyst is increased to 1.0 g and the propylene is replaced with styrene (20.8 g; 0.20 moles). Styrene oxide is the expected product.

EXAMPLE 9

A titanium-rich silicalite catalyst having a Si:Ti molar ratio of 17 is prepared in accordance with the teachings of Thangaraj et al., *J. Catal.* 130, 1 (1991) The procedure of Example 3 is repeated using this catalyst, with the exception that propylene is replaced with cyclohexene (16.4 g; 0.20 mole) and the reaction temperature is increased to 90° C. The expected product is cyclohexene oxide.

EXAMPLE 10

The procedure of Example 3 is repeated with the exception that the propylene is replaced with ethylene (5.6 g; 0.20 moles) and the α-methyl benzyl alcohol and acetophenone of the oxidant mixture are replaced by an equal volume of isopropanol. Ethylene oxide is the expected product.

EXAMPLE 11

The procedure of Example 3 is repeated with the exception that the propylene is replaced with 2,3-dimethyl-1-butene (16.8 g; 0.20 moles), the methanol, α-methyl benzyl alcohol, and acetophenone are replaced by an equal volume of t-butyl alcohol, and the reaction temperature is reduced to 50° C. The expected product is 2,3-dimethyl-1-butene oxide.

EXAMPLE 12

The procedure of Example 3 is repeated with the exception that the propylene is replaced by allyl phenyl ether (26.8 g; 0.20 mole)the reaction temperature is increased to 100° C., and the mixture is stirred for 60 minutes after addition of the oxidant mixture is completed. The expected product is phenyl glycidyl ether.

EXAMPLES 13-14

These examples demonstrate that selectivity to epoxide in an olefin epoxidation reaction is not adversely affected by the use of a titanium-rich silicalite catalyst, contrary to the expectation of the prior art teachings in this field.

An autoclave equipped as described in Example 3 was charged with methanol (25 mL), propylene (16 mL; 0.20 mole), and a titanium-rich silicalite catalyst having an MFI topology and containing 4.4 weight % titanium (0.73 g). The contents of the autoclave were heated to 80° C. before adding a mixture (100 mL) of α-methyl benzyl alcohol (70 weight %), acetophenone (25 weight %), and hydrogen peroxide (5 weight %; 0.14 mole) over a 38 sec. period. The autoclave was open to a reservoir of liquid propylene. The reaction mixture was stirred for 45 minutes at 80° C., yielding the results shown in Table I (Example 13).

The procedure described above was repeated, but with the substitution of a conventional titanium silicalite catalyst having an MFI topology and containing only 1.4 weight percent titanium (Comparative Example 14).

TABLE I

| Ex. No. | H$_2$O$_2$ Conversion, % | Epoxide Selectivity, % |
|---|---|---|
| 13 | 97 | 78 |
| 14* | 94 | 80 |

*Comparative example

Contrary to the expectation of the prior art, which teaches that poorer yields of epoxide products will result if a silicalite containing a relatively high titanium concentration is used, the practice of the process of this invention was found to produce epoxide at a selectivity equivalent to that obtained using a conventional silicalite epoxidation catalyst having a low titanium content.

We claim:

1. A process for producing an epoxide comprising contacting an olefin with a hydrogen peroxide source in the presence of a catalytically effective amount of a titanium silicalite zeolite having a Si:Ti molar ratio in the lattice framework of said zeolite of from 8:1 to 18:1 for a time and at a temperature effective to convert the olefin to epoxide.

2. The process of claim 1 wherein the crystalline titanium silicalite zeolite has an MFI or MEL topology.

3. The process of claim 1 wherein an organic solvent is additionally present during said contacting.

4. The process of claim 1 wherein said titanium silicalite zeolite is prepared using a solution of titanium tetrabutoxide dissolved in an anhydrous alcoholic medium.

5. The process of claim 1 wherein said titanium silicalite zeolite is prepared using a quaternary ammonium salt selected from tetrapropyl ammonium hydroxide, tetrabutyl ammonium hydroxide, methyltributyl ammonium hydroxide, trimethyl ethanol ammonium hydroxide, tetramethyl ammonium hydroxide, and mixtures thereof.

6. The process of claim 1 wherein the hydrogen peroxide source is produced by oxidation of an aryl-substituted secondary alcohol with molecular oxygen.

7. The process of claim 1 wherein the temperature is from 0° C. to 150° C.

8. The process of claim 1 wherein the olefin has the general formula

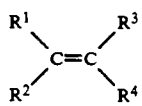

wherein R$^1$, R$^2$, R$^3$, and R$^4$ are the same or different and are selected from hydrogen, C$_1$–C$_{20}$ alkyl, C$_7$–C$_{20}$ aryl alkyl, C$_5$–C$_{12}$ cycloalkyl, C$_6$–C$_{20}$ alkyl cycloalkyl, and C$_6$–C$_{20}$ aryl.

9. The process of claim 1 wherein the amount of titanium silicalite zeolite is from 0.01 to 10 grams per mole of olefin.

10. The process of claim 1 wherein said process is conducted at a pressure of between 1 and 100 atmospheres.

11. The process of claim 1 wherein the Si:Ti molar ratio is from 9.5:1 to 18:1.

12. The process of claim 1 wherein the molar ratio of olefin:hydrogen peroxide source is from 1:10 to 10:1.

13. A process for producing an epoxide comprising contacting an olefin with a hydrogen peroxide source in the presence of an organic solvent and titanium silicalite zeolite having a Si:Ti molar ratio in the lattice framework of said zeolite of from 9.5:1 to 18:1 at a temperature of from 0° C. to 150° C. and for a time effective to convert the olefin to epoxide, wherein the amount of titanium silicalite zeolite is from 0.01 to 10 grams per mole of olefin and the molar ratio of olefin:hydrogen peroxide source is from 1:10 to 10:1.

14. The process of claim 13 wherein said organic solvent is selected from the group consisting of ketones, alcohols, and mixtures thereof.

15. The process of claim 13 wherein said organic solvent is an aryl-substituted secondary alcohol and the hydrogen peroxide source is produced by oxidation of the secondary alcohol with molecular oxygen.

16. The process of claim 13 wherein said organic solvent is selected from the group consisting of methanol, β-methylbenzyl, alcohol, isopropyl alcohol, cyclohexanol, acetophenone, acetone, and mixtures thereof.

17. The process of claim 13 wherein said zeolite has been treated with an acid-neutralizing agent selected from alkaline substances and silylating agents.

18. The process of claim 13 wherein said zeolite has an MFI or MEL topology.

19. The process of claim 13 wherein the olefin is selected from the group consisting of ethylene, propylene, 1-butene, 2-butene, 1-pentene, 2-pentene, allyl alcohol, allyl chloride, styrene, cyclohexene, alkyl phenyl ether, norbornene, isoprene, butadiene, isobutylene, 1-octene, vinyl cyclohexane and methallyl alcohol.

20. The process of claim 13 wherein the zeolite is prepared using a solution of titanium tetrabutoxide dissolved in an anhydrous alcoholic medium.

21. The process of claim 13 wherein the zeolite is prepared using a quaternary ammonium salt selected from tetrapropyl ammonium hydroxide, methyltributyl ammonium hydroxide, trimethyl ethanol ammonium hydroxide, tetramethyl ammonium hydroxide, tetrabutyl ammonium hydroxide, and mixtures thereof.

22. The process of claim 13 wherein said process is conducted at a pressure of between 1 and 100 atmospheres.

23. A process for producing propylene oxide comprising contacting propylene with hydrogen peroxide in the presence of a solvent selected from the group consisting of alcohols, ketones, and mixtures thereof and a titanium silicalite zeolite having a Si:Ti molar ratio in the lattice framework of said zeolite of from 9.5:1 to 18:1 and an MEL or MFI topology at a temperature of from 25° to 120° and for a time effective to convert the propylene to propylene oxide, wherein the amount of titanium silicalite zeolite is from 0.01 to 10 grams per mole of olefin and the molar ratio of olefin:hydrogen perioxide is from 1.05:1 to 1.57:1.

24. The process of claim 13 wherein said organic solvent is selected from the group consisting of acetone, isopropyl alcohol, and mixtures thereof.

* * * * *